United States Patent [19]

Vaughn

[11] Patent Number: 5,222,486
[45] Date of Patent: Jun. 29, 1993

[54] SWIVEL CONNECTOR FOR USE IN AN OXYGEN LINE

[75] Inventor: E. Lanny Vaughn, Pittsburg, Calif.

[73] Assignee: James Cromwell, Pittsburg, Calif. ; a part interest

[21] Appl. No.: 849,272

[22] Filed: Mar. 11, 1992

[51] Int. Cl.⁵ ............................................. A61M 39/00
[52] U.S. Cl. .......................... 128/200.24; 128/204.18; 128/207.18; 128/DIG. 26; 128/912; 285/98
[58] Field of Search ...................... 128/200.24, 202.27, 128/204.18, 207.18, 207.14, 911, 912, DIG. 26; 285/11, 98, 272

[56] References Cited

U.S. PATENT DOCUMENTS

| | | | |
|---|---|---|---|
| 2,820,651 | 1/1958 | Phillips | 128/204.18 X |
| 3,504,935 | 4/1970 | Gullihur | 285/98 X |
| 3,510,155 | 5/1970 | Jacobus | 285/98 |
| 3,972,321 | 8/1976 | Proctor | 128/DIG. 26 X |
| 4,152,017 | 1/1979 | Abramson | 128/207.14 X |
| 4,588,402 | 5/1986 | Igari | 604/408 |
| 4,633,890 | 1/1987 | Carden | 128/910 |
| 4,676,241 | 6/1987 | Webb | 128/207.14 |
| 4,852,563 | 8/1989 | Gross | 128/202.27 |
| 4,915,104 | 4/1990 | Marcy | 128/207.18 |
| 5,062,420 | 11/1991 | Levine | 128/204.18 |
| 5,092,854 | 3/1992 | Black | 604/243 |
| 5,116,088 | 5/1992 | Bird | 285/319 |

FOREIGN PATENT DOCUMENTS

| | | | |
|---|---|---|---|
| 2026118 | 1/1980 | United Kingdom | 285/98 |
| 2169515 | 7/1986 | United Kingdom | 128/207.14 |

OTHER PUBLICATIONS

*Manufacturing Processes*, Roberts & Capidge, McGraw-Hill, 1977, p. 49, "Fits".

Primary Examiner—Edgar S. Burr
Assistant Examiner—Eric P. Raciti
Attorney, Agent, or Firm—Bruce H. Johnsonbaugh

[57] ABSTRACT

A swivel connector is provided for use in an oxygen line to prevent kinking of the oxygen line. The swivel connector has a body with an elongated cylindrical cavity adapted to receive an elongated hollow sleeve. The hollow sleeve has a flange near the end of the sleeve that is inserted into the cavity. A press fit keeper connects firmly to the body and has an inner bore which encircles the sleeve but which provides clearance between the keeper and the sleeve. An O-ring seal is provided between the sleeve and the body. The sleeve is therefore able to freely rotate relative to the body, preventing the oxygen hose from kinking.

3 Claims, 1 Drawing Sheet

SWIVEL CONNECTOR FOR USE IN AN OXYGEN LINE

BACKGROUND

This invention relates generally to a swivel connector for use in an oxygen line to prevent the line from kinking.

The prior art includes U.S. Pat. No. 4,875,718 dated Oct. 24, 1989 to Marken, which teaches a ball and socket swivel connector for oxygen lines. However, the ball and socket joint of Marken relies on a fairly close fit between the ball and socket to prevent leakage of oxygen. The tighter the fit between the ball and socket, the more difficult it is for the mechanism to swivel. Furthermore, both ends of the ball and socket connector may rotate if the friction between the ball and socket is sufficiently great. The present invention provides a swivel connector in which oxygen leakage is held to a minimum but wherein the swivel is allowed to rotate freely, because a relatively small surface area is involved in the sealing mechanism of the present invention. Furthermore, the present invention provides a clip attached to the user's clothing which prevents rotation of the body portion of the connector.

The prior art also includes U.S. Pat. No. 4,915,104 dated Apr. 10, 1990 to Marcy. This patent teaches a nasal oxygen tube support which includes a clip used to help support a part of the oxygen tubing. However, this patent does not teach a swivel connector.

The prior art also includes U.S. Pat. No. 5,054,482 dated Oct. 8, 1991 to Bales. This patent teaches a rotatable tracheostomy tube which does include a rotatable connector. However, this connector is extremely cumbersome in design, particularly as applied in an oxygen line.

BRIEF SUMMARY OF THE INVENTION

The present invention provides a very simple but extremely effective swivel connector for an oxygen line. The mechanism has a relatively small area of contact between the components that are sealed relative to each other which allows for the swivel to rotate freely with the lightest rotational pressure applied. The swivel connector, according to the present invention, also provides a virtually foolproof keeper design which keeps the connector from coming apart and, thus, interrupting the flow of oxygen. The present design also provides a clip which helps support the weight of the connector but which also prevents rotation of the upper half of the connector relative to the body of the user.

Accordingly, a primary object of the invention is to provide a small but effective swivel connector for use in oxygen lines which freely rotates with the slightest rotation pressure applied.

Another object of the invention is to provide a swivel connector for use in oxygen lines which is highly resistant to coming apart and interrupting the flow of oxygen.

Another object of the invention is to provide a swivel connector for oxygen lines which is very inexpensive.

A further object of the invention is to provide a swivel connector for oxygen lines which is autoclavable.

Yet another object of the invention is to provide a swivel connector for oxygen lines having a clip attachable to the user's clothing to support the weight of the oxygen line and which prevents the upper portion of the connector from rotating relative to the user's body.

Other objects and advantages of the invention will become apparent from the following description of the preferred embodiment and the drawings wherein:

DETAILED DESCRIPTION OF THE DRAWINGS

Figures 1, 2, 3:
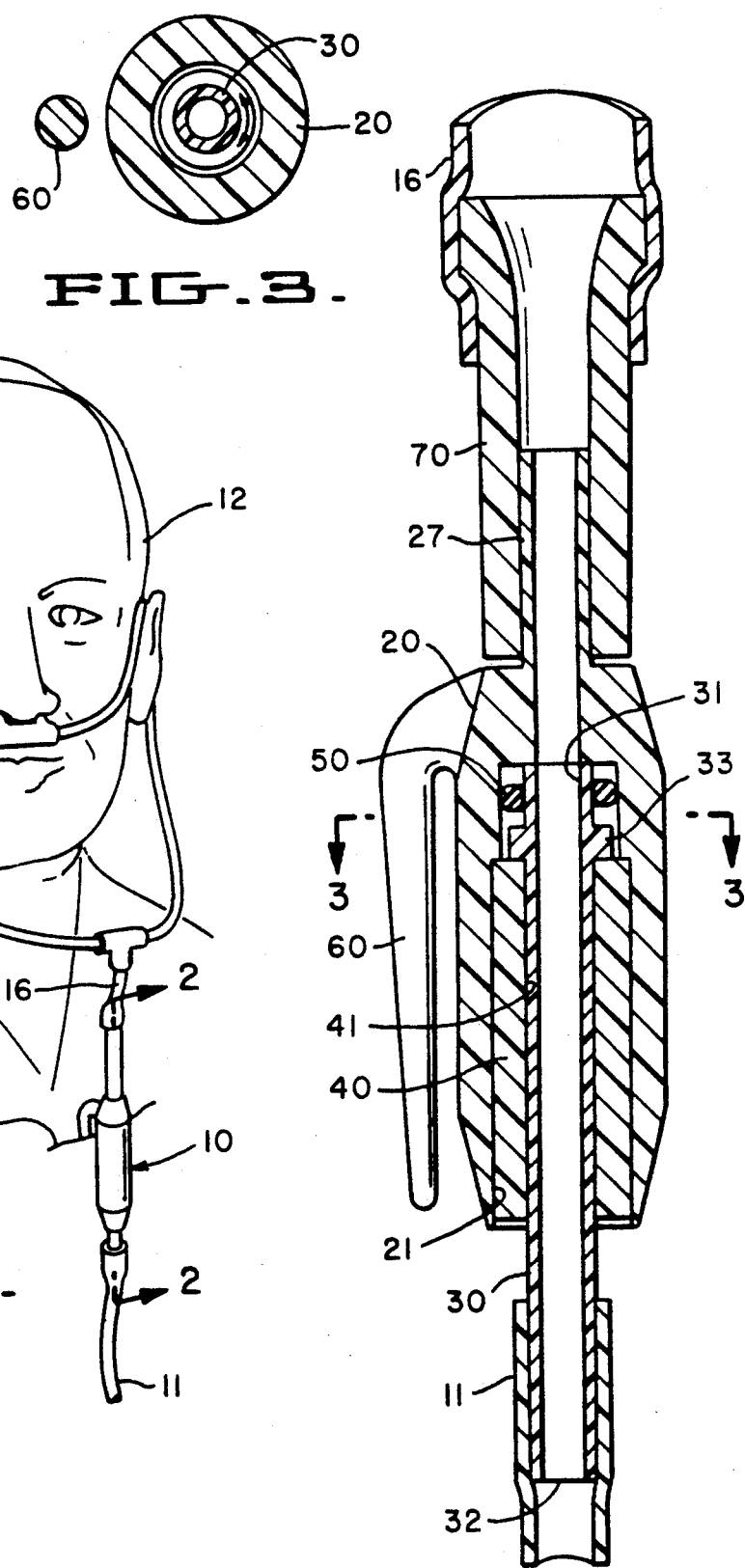
FIG. 1 is a perspective view showing the swivel connector of the present invention shown being worn by a user.
FIG. 2 is a section on the line 2—2 of FIG. 1.
FIG. 3 is a section on the line 3—3 of FIG. 2.

As shown in FIG. 1, swivel connector shown generally as 10 is provided for use in an oxygen line 11 which typically carries oxygen to the user 12 through a nasal feed 13. The swivel connector 10 is provided to allow free rotation of oxygen line 11 relative to swivel connector 10 as the user 12 moves about.

Referring to FIG. 2, a body 20 is provided which is generally cylindrical in design and which is somewhat elongated. An elongated, cylindrical cavity 21 is formed in body 20.

An elongated hollow sleeve 30 is provided which has a first end 31 and a second end 32. A flange 33 is formed near first end 31. Hollow sleeve 30 is adapted to slide into cavity 21 of body 20.

An elongated hollow keeper 40 is provided which is cylindrical in design and which is adapted to be press fit into cavity 21 so that keeper 40 and body 20 are firmly held together, which prevents keeper 40 from being pulled out of body 20, which could result in interruption of the oxygen supply. Keeper 40 has an inner cylindrical bore 41 which encircles sleeve 30. Bore 41 has a sufficiently large diameter to provide clearance relative to sleeve 30. This clearance is approximately 0.005 inch and allows sleeve 30 to rotate freely with respect to keeper 40 in response to the slightest rotation of oxygen line 11.

Flange 33 has a sufficiently large diameter and directly faces an end of keeper 40 to prevent the sleeve 30 from being pulled outwardly from cavity 21, which would otherwise interrupt the flow of oxygen.

A sealing means 50, which in FIG. 2 comprises an O-ring, is carried by a projecting portion of sleeve 30 which extends beyond flange 33 to the first end 31 of sleeve 30 and the O-ring seals the sleeve 30 relative to the body 20.

A clip means 60 is also provided which is rigidly connected to body 20 and is adapted to being connected to an article of clothing such as a shirt 61 worn by the user 12. Clip 60 also serves to prevent rotation of the body portion of the swivel connector relative to the user 12.

The upper portion of body 20 may be provided with an adapter 70 which frictionally engages the upper outlet 27 of body 20. Adapter 70 in turn frictionally engages oxygen line 16 which in turn transmits oxygen to nasal feed 13.

The components of the swivel connector shown may be made of autoclavable plastic. As an alternative method of use, the device is sufficiently inexpensive that it can be used on a disposable basis, as opposed to being sterilized and reused.

What is claimed is:

1. A swivel connector for use in an oxygen line to prevent said oxygen line from kinking, comprising:

a body having an elongated, cylindrical cavity formed therein, an elongated, hollow sleeve having first and second ends and a flange near said first end, said sleeve being slidable in said cavity in said body, an elongated, hollow keeper press fitted into said cylindrical cavity of said body so that said keeper and said body are permanently and firmly held together, said keeper having an inner, cylindrical bore which encircles said sleeve, said bore being of sufficiently large diameter to provide clearance relative to said sleeve, said clearance being sufficiently large to minimize contact between said keeper and said sleeve to allow said sleeve to rotate freely relative to said keeper and relative to said body, said flange directly facing an end of said keeper and having a sufficiently large diameter to prevent said sleeve from being pulled outwardly from said cavity, and sealing means carried by said first end of said sleeve for sealing said sleeve relative to said body, said sleeve including a projecting portion extending beyond said flange to said first end, said sealing means comprising a sealing ring on said projecting portion, said sealing ring having a cross-sectional extent less than the length of said projecting portion.

2. The apparatus of claim 1 further comprising clip means rigidly connected to said body, said clip means adapted to being connected to an article of clothing worn by the user, said clip means also serving to prevent rotation of said body.

3. The apparatus of claim 1 wherein said sealing ring comprises an O-ring.

* * * * *